(12) United States Patent  
Gonnelli et al.

(10) Patent No.: US 8,162,901 B2
(45) Date of Patent: Apr. 24, 2012

(54) MICRONEEDLE ARRAY PATCH (75) Inventors: Robert R. Gonnelli, Mahwah, NJ (US); Devin V. McAllister, Shrewsbury, MA (US)

(73) Assignee: Valeritas, Inc., Bridgewater, NJ (US)

( * ) Notice: Subject to any disclaimer, the term of this patent is extended or adjusted under 35 U.S.C. 154(b) by 0 days.

(21) Appl. No.: 11/975,717

(22) Filed: Oct. 19, 2007

(65) Prior Publication Data

US 2009/0118672 A1 May 7, 2009

Related U.S. Application Data (63) Continuation of application No. 10/681,777, filed on Oct. 7, 2003, now abandoned.

(60) Provisional application No. 60/416,740, filed on Oct. 7, 2002.

(51) Int. Cl.
*A61M 5/315* (2006.01)
(52) U.S. Cl. ......... 604/246; 604/151; 604/180; 604/181
(58) Field of Classification Search .............. 604/46–47, 604/180, 151, 181, 186–187, 191, 236–238, 604/246
See application file for complete search history.

(56) References Cited

U.S. PATENT DOCUMENTS

| | | |
|---|---|---|
| 2,522,309 A | 9/1950 | Simon |
| 3,289,675 A | 12/1966 | Eby et al. |
| 3,964,482 A | 6/1976 | Gerstel et al. |
| 4,324,236 A | 4/1982 | Gordon et al. |
| 4,685,903 A | 8/1987 | Cable et al. |
| 4,936,835 A * | 6/1990 | Haaga ........................ 604/265 |
| 5,279,544 A | 1/1994 | Gross et al. |
| 5,569,272 A | 10/1996 | Reed et al. |
| 5,697,901 A | 12/1997 | Eriksson |
| 5,820,570 A | 10/1998 | Erickson et al. |
| 5,931,794 A | 8/1999 | Pitesky |
| 6,020,208 A | 2/2000 | Hutchens et al. |

(Continued)

FOREIGN PATENT DOCUMENTS

WO WO-97/48440 12/1997

(Continued)

OTHER PUBLICATIONS

Strong, et al., Phosphorylation state of the native high-molecular-weight neurofilament subunit protein from cervical spinal cord in sporatic amyotrophic lateral sclerosis. J. Neurochem. 76: 1315-1325, 2001.

(Continued)

*Primary Examiner* — Theodore Stigell
(74) *Attorney, Agent, or Firm* — Morse, Barnes-Brown & Pendleton, P.C.; Lisa M. Treannie, Esq.

(57) ABSTRACT

Microneedle devices for transport of molecules, including drugs and biological molecules, across tissue, are provided. The microneedle devices permit drug delivery or removal of body fluids at clinically relevant rates across skin or other tissue barriers, with minimal or no damage, pain, or irritation to the tissue. Microneedles can be formed of biodegradable or non-biodegradable polymeric materials or metals. In a preferred embodiment, a microneedle device includes a plugging element comprising a platform including a plurality of microneedle plugs for preventing skin or other tissue barriers from entering the hollow microneedles. In another preferred embodiment, a microneedle device includes a plurality of bioerodible elements for temporarily plugging the hollow microneedles, thereby preventing skin or other tissue barriers from entering the hollow microneedles.

15 Claims, 7 Drawing Sheets

U.S. PATENT DOCUMENTS

| | | | |
|---|---|---|---|
| 6,083,196 A | 7/2000 | Trautman et al. | |
| 6,132,755 A | 10/2000 | Eicher et al. | |
| 6,183,434 B1 | 2/2001 | Epstein | |
| 6,230,051 B1 | 5/2001 | Cormier et al. | |
| 6,256,533 B1 | 7/2001 | Yuzhakov et al. | |
| 6,271,037 B1 | 8/2001 | Chait et al. | |
| 6,293,925 B1 | 9/2001 | Safanash et al. | |
| 6,329,146 B1 | 12/2001 | Crooke et al. | |
| 6,334,856 B1 | 1/2002 | Allen et al. | |
| 6,440,096 B1 | 8/2002 | Lastovich et al. | |
| 6,503,231 B1 | 1/2003 | Prausnitz et al. | |
| 6,537,242 B1 | 3/2003 | Palmer | |
| 6,558,361 B1 | 5/2003 | Yeshrun | |
| 6,591,124 B2 | 7/2003 | Sherman et al. | |
| 6,603,998 B1 | 8/2003 | King et al. | |
| 6,611,707 B1 | 8/2003 | Prausnitz et al. | |
| 6,623,457 B1 | 9/2003 | Rosenberg | |
| 6,629,949 B1 * | 10/2003 | Douglas | 604/46 |
| 6,656,147 B1 | 12/2003 | Gertsek et al. | |
| 6,695,859 B1 | 2/2004 | Golden et al. | |
| 6,713,291 B2 | 3/2004 | King et al. | |
| 6,743,211 B1 | 6/2004 | Prausnitz et al. | |
| 6,767,341 B2 | 7/2004 | Cho | |
| 6,780,171 B2 | 8/2004 | Gabel et al. | |
| 6,837,988 B2 | 1/2005 | Leong et al. | |
| 6,899,717 B2 | 5/2005 | Weber et al. | |
| 2001/0053891 A1 | 12/2001 | Ackley | |
| 2002/0010412 A1 | 1/2002 | Eppstein | |
| 2002/0082543 A1 | 6/2002 | Park et al. | |
| 2003/0135201 A1 * | 7/2003 | Gonnelli | 604/890.1 |

FOREIGN PATENT DOCUMENTS

| | | |
|---|---|---|
| WO | WO-97/48441 | 12/1997 |
| WO | WO-97/48442 | 12/1997 |
| WO | WO-98/00193 | 1/1998 |
| WO | WO-01/49346 | 7/2001 |

OTHER PUBLICATIONS

Rossomando et al., Identification of Tyr-185 as the Site of Tyrosine Autophosphorylation of Recombinant Mitogen-Activated protein Kinase p42$^{mapk}$. Proc. Natl. Acad. S 89: 5779-5783, 1992.

Non-Final Office Action for U.S. Appl. No. 10/681,777, dated Apr. 19, 2007.

Final Office Action for U.S Appl. No. 10/681,777, dated Mar. 23, 2006.

Non-Final Office Action for U.S. Appl. No. 10/681,777, dated Jun. 14, 2005.

\* cited by examiner

MICRONEEDLE ARRAY PATCH

RELATED APPLICATIONS

This application is a continuation application of U.S. Ser. No. 10/681,777 (now abandoned), filed on Oct. 7, 2003, which claims the benefit of the filing date under 35 U.S.C. § 119(e) to US Provisional Application 60/416,740, filed on Oct. 7, 2002, entitled Microneedle Array Patch, the contents of which are herein incorporated by reference.

BACKGROUND

This invention relates to injection devices, such as microneedle devices having an array of microneedles for placing on the skin.

Conventional methods of biological fluid sampling and non-oral drug delivery are normally invasive. That is, the skin is lanced to extract blood and measure various components when performing fluid sampling, or a drug delivery procedure is normally performed by injection, which causes pain and requires special medical training. Alternatives to drug delivery by injection have been disclosed, for example, by Henry, McAllister, Allen, and Prausnitz, of Georgia Institute of Technology (in a paper titled "Micromachined Needles for the Transdermal Delivery of Drugs"), U.S. Pat. No. 3,964,482, WO 98/00193, WO 97/48440, WO 97/48441, and WO 97/48442.

The use of microneedles has great advantages in that intracutaneous drug delivery can be accomplished without pain, leading to increased patient compliance, and without bleeding. Further, patients may apply the drug delivery devices themselves without extensive training. As used herein, the term "microneedles" refers to a plurality of elongated structures that are sufficiently long to penetrate through the stratum corneum skin layer and into the epidermal layer, yet are also sufficiently short to not penetrate to the dermal layer. However, if the dead cells have been completely or mostly removed from a portion of skin, then a very minute length of microneedle could be used to reach the viable epidermal tissue.

However, technical problems exist in the use of such microneedles. Among them is the plugging of hollow microneedles with skin or other tissues, thus, preventing the flow of therapeutic through the microneedle. This may have an impact on the amount of therapeutic actually delivered to the patient, which can be important for proper dosing.

SUMMARY OF THE INVENTION

Microneedle devices for transport of molecules, including drugs and biological molecules, across tissue, are provided. The microneedle devices permit drug delivery or removal of body fluids at clinically relevant rates across skin or other tissue barriers, with minimal or no damage, pain, or irritation to the tissue. Microneedles can be formed of a variety of materials, including biodegradable or non-biodegradable polymeric materials or metals. The microneedle devices described herein include a hollow microneedle capable of penetrating the stratum corneum. The microneedle has a movable barrier located at a distal end of the microneedle. The moveable barrier prevents or reduces tissue from blocking an interior channel that extends though the microneedle. In one particular embodiment, the microneedle device include a platform or substrate having a plurality of microneedles each with plugs disposed at their distal ends for preventing skin or other tissue barriers from entering the hollow microneedles. In another embodiment, a microneedle device includes a plurality of bioerodible elements for temporarily plugging the hollow microneedles, thereby preventing skin or other tissue barriers from entering the hollow microneedles. The bio erodible elements may be plugs that are fitted within the distal end of a channel extending through the microneedle. The plugs may be frangible and optionally may have a seam that allows the plug to separate from the microneedle. Once separated the plug may dissolve over time.

In a further optional embodiment, the devices described herein may include moveable barriers that comprise pins or pistons that fit within the interior channels of the microneedle and may be moved through the channel so that a distal portion of the pin or piston sits within the distal end of the channel and prevents tissue from blocking the microneedle. In a further optional embodiment, the pin or piston may be capable of pushing tissue from the channel to dislodge any tissue blocking the channel.

Additional advantages and other novel features of the invention will be set forth in part in the description that follows and in part will become apparent to those skilled in the art upon examination of the following or may be learned with the practice of the invention. As will be realized, the invention is capable of other different embodiments, and its several details are capable of modification in various, aspects all without departing from the invention. Accordingly, the drawings and descriptions will be regarded as illustrative in nature and not as restrictive.

DETAILED DESCRIPTION OF EXEMPLARY EMBODIMENTS

The systems and methods described herein are, in one aspect, directed to transdermal devices, including an intraepidermal delivery devices for administering a substance to a patient. More particularly, the invention is directed to devices and to methods for establishing fluid communication for administering agents and monitoring a patent's condition. In one exemplary embodiment the systems and methods provide delivery devices for administering a substance into or below the stratum corneum of the skin of a patient. As used herein, the term penetrate refers to entering a layer of the skin without necessarily passing completely through. Piercing refers to passing completely through a layer of the skin. As used herein, transdermal refers to the exchange of a substance, such as blood, a pharmaceutical, a biological agent or a vaccine, through one or more layers of skin. Intradermal refers to one or more layers within the skin and not limited to the dermis layer of the skin.

The devices and methods are particularly suitable for use in administering various substances, including pharmaceutical agents, to a patient, and notably to a human patient. A pharmaceutical agent includes a substance having biological activity that can be delivered through the body membranes and surfaces, and particularly the skin. Examples include antibiotics, antiviral agents, analgesics, anesthetics, anorexics, antiarthritics, antidepressants, antihistamines, anti-inflammatory agents, antineoplastic agents, vaccines, including DNA vaccines, adjuvants, biologics, and the like. Other substances which can be delivered intradermally to a patient include proteins, peptides and fragments thereof. The proteins and peptides can be naturally occurring, synthesized or recombinantly produced.

In some embodiments, a vaccine is administered using the device and method. The multipuncture devices of described herein are believed in addition to have a unique immunological advantage in the delivery of vaccines with the potential of increasing the vaccine's clinical value. The insertion of the multiple needle points into the tissue is suggested as having an adjuvant-like stimulatory effect. The needle stick response from multiple microneedle points is believed more than a simple acute inflammatory response. Needle sticks can cause damage to a variety of cells and cellular architecture, causing the appearance of polymorphonuclear neutrophil (PMN) and microphages as well as the release of cytokines, including ILI, tumor necrosis factor (TNF) and other agents, which can lead to a number of other immunological responses. The soluble stimulatory factors influence the proliferation of lymphocytes and are central to the immune response to vaccines. The immune stimulation is proportional to the direct needle-cell interaction.

The microneedle device is valuable in promoting significant immune response to a vaccine by delivering a vaccine below the stratum corneum and into the cells of the tissue. Some of the microneedles can have a length selected to penetrate and pass through the stratum corneum without penetrating the dermis to minimize absorption of the vaccine into the bloodstream. The small intracellular depots created by the microneedle array are believed to increase the availability of the vaccine antigen for interaction with antigen presenting cells more than would a vaccine deposited by standard needles in a larger depot quantity. In further embodiments, some or all of the microneedles can have a length to penetrate, but not pierce, the stratum corneum.

The microneedle array is believed to magnify several-fold the trivial or inconsequential immune stimulatory impact of a single needlestick independent of the route of delivery and vaccine. The microneedle delivery device facilitates and enhances vaccine immunogenicity by an adjuvant-like immune stimulation.

The primary barrier properties of the skin including the resistance to drug penetration reside in the outermost layer of the skin, referred to as the stratum corneum. The inner layers of the epidermis generally include three layers, commonly identified as the stratum granulosum, the stratum malpighii, and the stratum germinativum. Once a drug or other substance penetrates below the stratum corneum, there is substantially less resistance to permeation into the subsequent layers of the skin and eventual absorption by the body. Thus, delivery of a substance below the stratum corneum can be an effective system for administering some substances, and particularly some vaccines, to the body. The devices and methods described herein will, among other things, for deliver a substance, and particularly a pharmaceutical agent, into or below the stratum corneum for administering the substance or pharmaceutical agent to the patient. Preferably, the device and method pierce the stratum corneum substantially without penetrating the dermis to target the tissue layers below the stratum corneum. It is of potential benefit for vaccines to target presentation of antigen to various antigen presenting cells and other immunostimulatory sites, such as Langerhans cells and intraepithelial cells, as well as proximal delivery of adjuvants.

Figure 1:
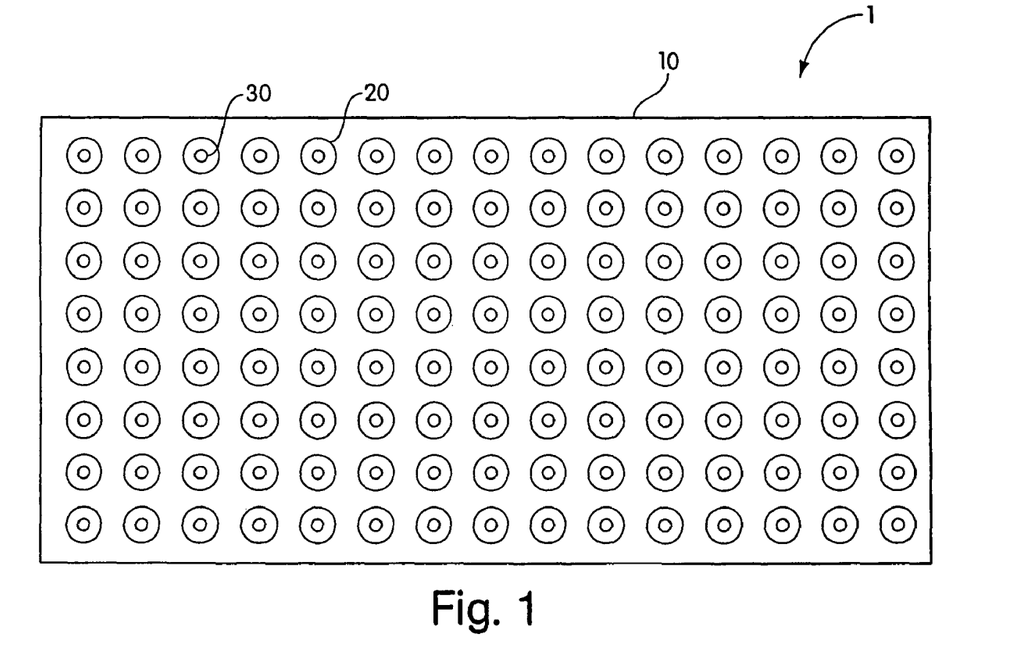
FIG. 1 depicts a microneedle surface of one embodiment of the invention.

FIG. 1 depicts one embodiment of a microneedle device. Microneedle device 1 shows microneedle surface 10, including microneedles 20 with microneedles openings 30. As shown, the microneedle device may comprise an array of microneedles, each of which is hollow and each of which can penetrate the stratum corneum. In this embodiment, the microneedle array may be used as part of a transdermal patch that transdermally delivers a substance to the patient or transdermally collects a sample from the patient. To this end the device 1 may include a reservoir that can store a fluid substance or substances to deliver to the patient or that was collected from the patient. In either case, and as will be described in more detail herein, the microneedle device 1 includes a distal barrier over or within one or more of the microneedles 20, and typically, the barrier is disposed over or within the distal end of the channel 30 to prevent tissue from blocking the channel openings 30 when the patient or doctor applies pressure to device 1 to force the microneedles 20 through the tissue.

Figure 2A:
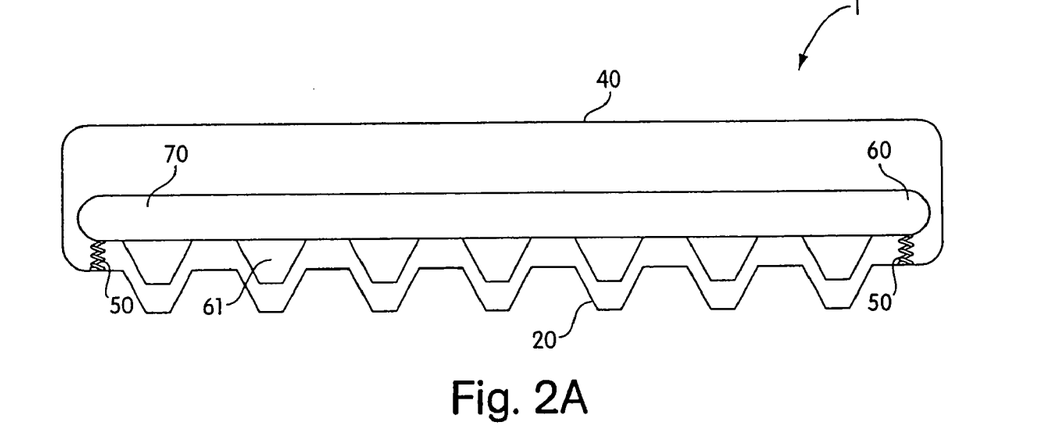
FIG. 2A depicts a cross-sectional view of the microneedle device of FIG. 1 in its resting state.

FIG. 2A depicts a cross-sectional view of microneedle device 1 in its resting state. Drug reservoir 70 is loaded with a predetermined amount of a therapeutic in liquid form. Platform 60 includes microneedle plugs 61 which are arrayed to fit into microneedles 20 in order to prevent punctured skin from entering and plugging microneedles 20, and preventing the release of therapeutic. Platform 60 rests on springs 50 which hold platform 60 and microneedle plugs 61 above microneedles 20.

Figure 2B:
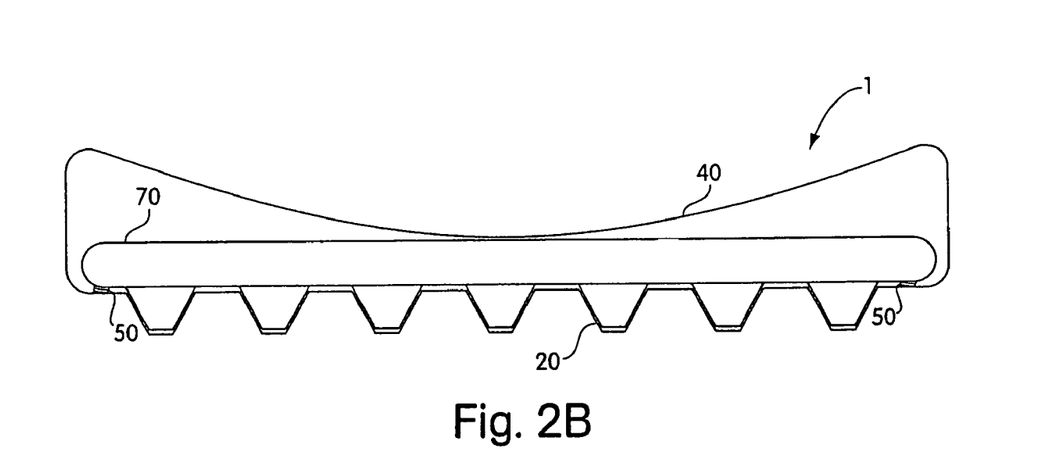
FIG. 2B depicts a cross-sectional view of the microneedle device of FIG. 1 when pressure is applied to back of the patch.

FIG. 2B depicts a cross-sectional view of microneedle device 1 when pressure (represented by three arrows) is applied to device surface 40 while microneedle device 1 is being applied to skin. Microneedle device 1 is applied to skin with microneedle surface 10 in contact with the skin. The pressure pushes down platform 60 depresses springs 50, and forces microneedle plugs 61 into microneedles 20, preventing skin from entering and plugging microneedles 20. After pressure is released from device surface 40, device 1 returns to the formation shown in FIG. 2A. Springs 50 re-extend to lift platform 60 and microneedle plugs 61 from microneedles 20. At this point, microneedles 20 are embedded into skin and the therapeutic in a liquid composition or form escapes from drug reservoir 70 through microneedles openings 30. Thus the plugs 61 act as moveable barriers that prevent tissue from blocking the openings 30 of microneedles 20.

Platform 60 is depicted in FIGS. 2A-2B as solid, however, other embodiments are contemplated. For example, platform 60 may include a plurality of openings, in the areas surrounding platform plugs 61, through which a therapeutic may flow from drug reservoir 70 through microneedles 20. Further, FIGS. 2A-2B depict the interior microneedle 61 (as being sized to fit within the interior of microneedles 20. However, in other embodiments, the microneedles 20 may have narrow interior channels and in this embodiment microneedle 61 may be narrow pin shaped elements that may slide into, and optionally extend from, the distal opening of the microneedles 20. In either case the plugs 61 do not need to have interior channels for passing fluid as microneedles may be slid out of, at least partially, the interior channel of the microneedle 20. In such embodiments, the conical shape of the microneedle interior channel will provide space between the plugs 61 and the interior wall of the conical channel, thereby providing a space through which the therapeutic fluid may flow. In further optional embodiments, the plugs 61 may have an exterior surface that is grooved or scored to provide a path through which liquid may flow. Optionally, the wall of the interior channel may be similarly grooved or scored. Other techniques for increasing fluid flow may be practiced with the systems described herein without departing from the scope of the invention.

Figure 3:
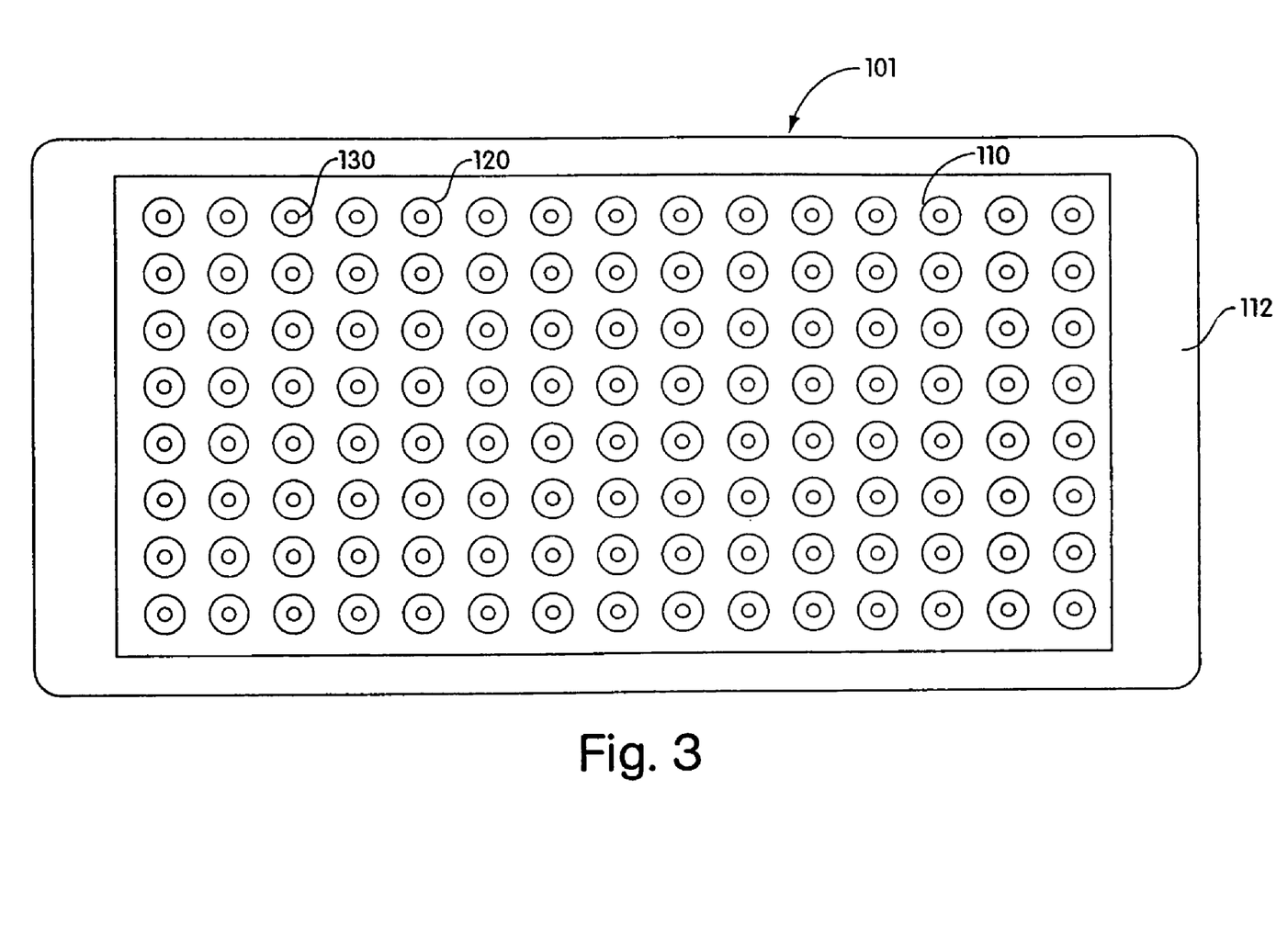
FIG. 3 depicts a microneedle surface of a different embodiment of the invention.

FIG. 3 depicts an alternative embodiment of a microneedle device. Microneedle device 101 shows microneedle surface 110, including microneedles 120 with microneedle plugs 130. An optional adhesive patch 112 secures the device 101 to the tissue of the patient.

Figure 4A:
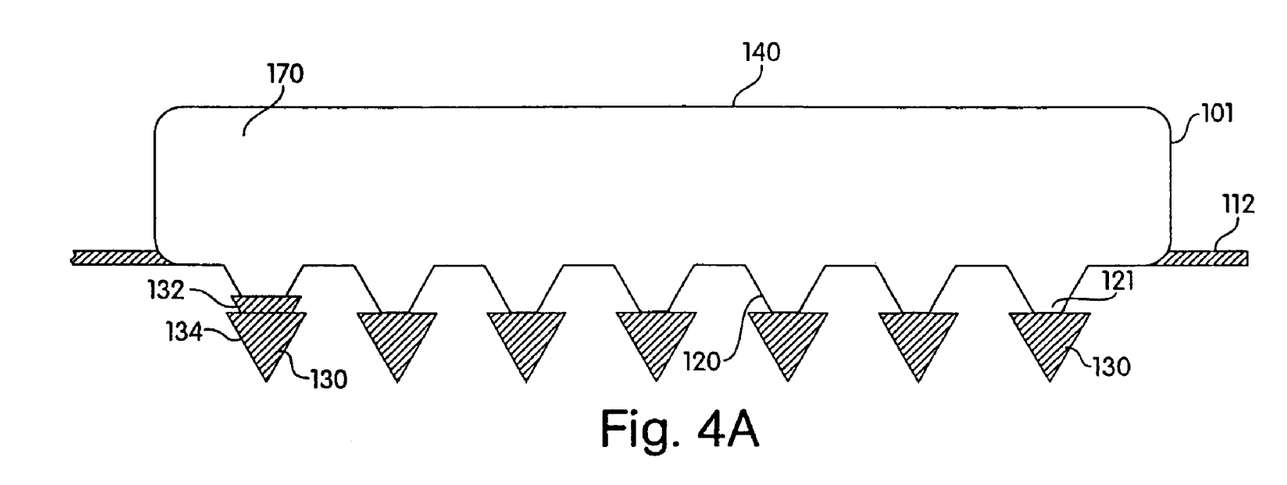
FIG. 4A depicts a cross-sectional view of the microneedle device of FIG. 3 prior to its application to skin.

FIG. 4A depicts a cross-sectional view of microneedle device 101 prior to its application to skin. In this embodiment, drug reservoir 170 is loaded with a predetermined amount of a therapeutic in liquid form. The microneedle openings 121 of microneedles 120 are blocked by microneedle plugs 130. Microneedle plugs 130 have an arcuate shape with shoulders 132 that extend beyond the diameter of microneedles 120. In this embodiment, the plugs 130 have a shape adapted to act as a barb and catch biological tissue. The plugs 130 may have a frangible seam that fractures when the microneedle device 101 is applied to the patient's tissue. This allows the plug 130 to separate from the needle 120, and thereby facilitates the flow of agent through the needle 120.

Figure 4B:
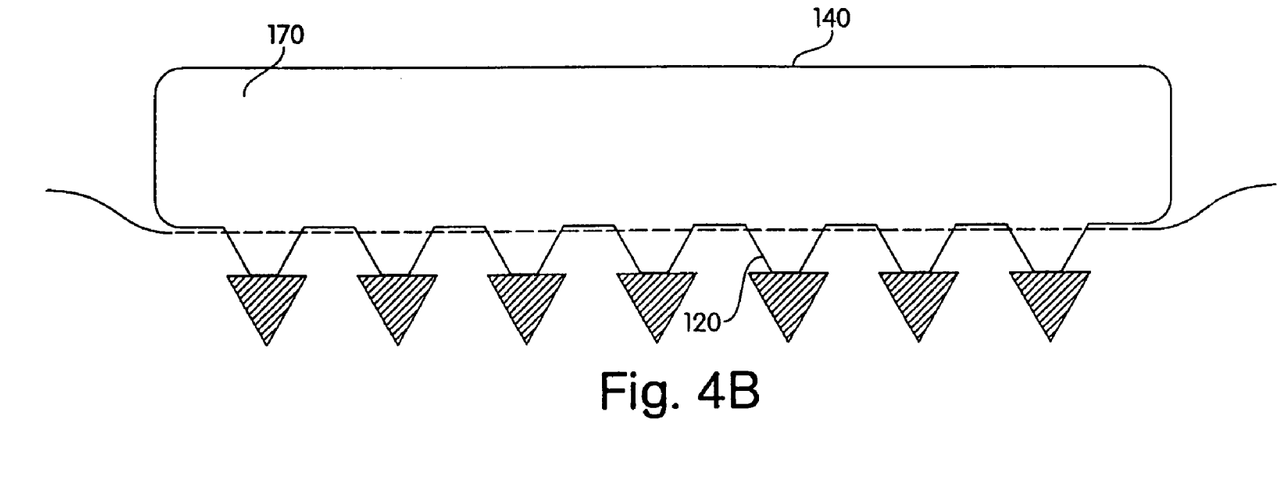
FIG. 4B depicts a cross-sectional view of the microneedle device of FIG. 3 during its application to skin.

FIG. 4B depicts a cross-sectional view of the microneedle device 101 during its application to skin. Microneedle device 101 is applied to skin with microneedle surface 110 in contact with the skin. Microneedle plugs 130 block microneedles openings 121, preventing skin from entering and plugging microneedles 120, thereby preventing the release of therapeutic. Microneedle device 101 is pressed into skin to a deeper level than when the pressure applied to microneedle device 101 is released. When the pressure is released, microneedle device 101 rises from the level it has been pushed to and rests on the surface of the skin. However, shoulders 132 of microneedle plugs 130 anchor microneedle plugs 130 at the level to which microneedle plugs 130 have been pushed. Thus, as microneedle device 101 rises to rest on the surface of the skin, microneedle plugs 130 are pulled out of microneedle openings 121 and microneedles 120.

Figure 4C:
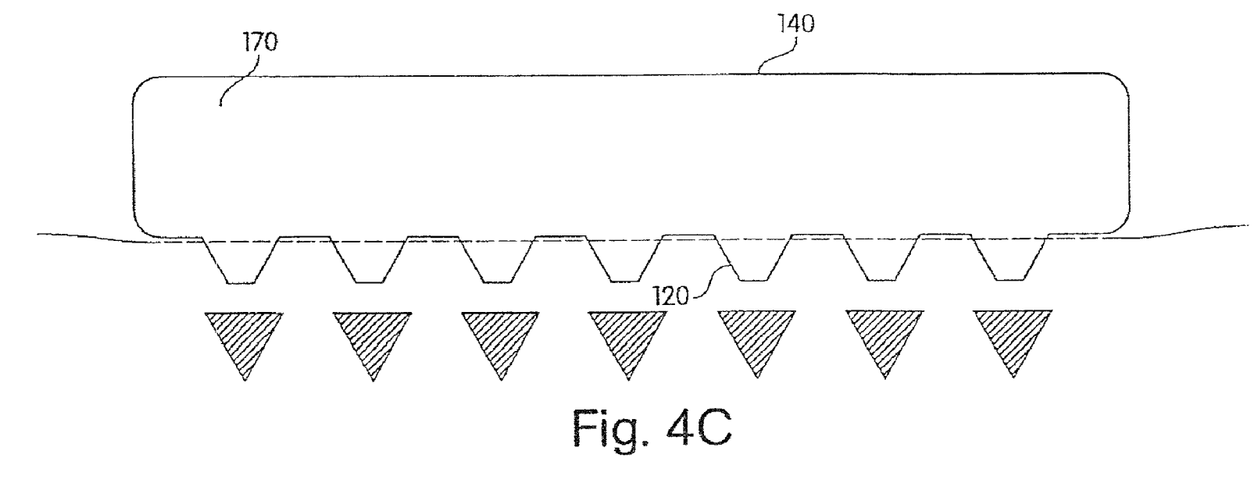
FIG. 4C depicts a cross-sectional view of the microneedle device of FIG. 3 after its application to skin.

FIG. 4C depicts a cross-sectional view of microneedle device 101 after its application to skin and microneedle plugs 130 are anchored in skin. The therapeutic in a liquid composition or form escapes from drug reservoir 170 through microneedles openings 121. The anchored plugs 130 may be comprised of a biologically erodible material that over time will dissolve. Optionally and alternatively, the plugs 130 may comprise a therapeutic material that carries a medicant into the patient's tissue to provide a time release dose that may work in cooperation with the fluidic medicant delivered through the microneedles 120.

Figure 4D:
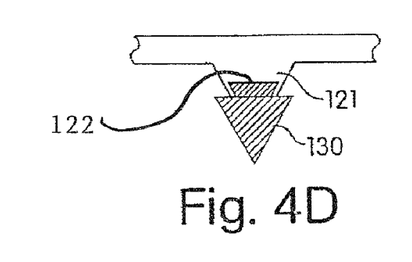
FIG. 4D depicts a cross-sectional view of a microneedle and plug.

FIG. 4D depicts a cross-sectional view of the microneedle 120 having a plug 130 disposed therein. Specifically, FIG. 4D depicts that the microneedle 120 may have an interior channel 122 that is conically shaped. The plug 130 may have a lower arcuate section and an upper conical section. The upper conical section mates up with the interior wall of the channel 122 to form a mechanical stop that prevents the plug 130 from sliding out of the distal end of the interior channel 122. In a further optional embodiment, the plug 130 may include a proximal end that secures to the exterior surface of the microneedle 120. In such an embodiment, the plug 130 does not enter into the microneedle channel, or does not enter a substantial amount. Instead the plug 130 includes a frangible collar that wraps around and secures to the exterior distal surface of the microneedle 120. Such an embodiment is depicted in FIG. 4A which shows one of the microneedles 130 having a proximal collar. The proximal collar may be formed of the same material as the plug 130, or optionally of a different material. A frangible seam 134, which may be a perforated seam, may be disposed between the collar and the distal end of the plug 130. The frangible seam 134 may facilitate the separation of the distal end of the plug 130 from the device 101. In these embodiments, the plug 130 may be formed of a bioerodible material. Such materials include polymers of hydroxy acid and are enumerated in more detail below. In other embodiment, the plug 130 may be made of other materials, including materials that carry a medicant for delivering medicant to the patient. Still, in other embodiments, the plug 130 may include a combination of materials. In any case, the material or materials selected will depend upon the application at hand and all are understood to fall within the scope of the invention.

Microneedle device 1 or 101 can be used as a continuous non-invasive medical device that continuously delivers a fluidic drug through the skin and into the body. Microneedle device 1 or 101 is applied to the skin such that microneedles 20 or 120 penetrate through the stratum corneum and enter the viable epidermis so that the tip of microneedles 20 or 120 at least penetrates into the viable epidermis. For one example, insulin could be delivered to the blood stream via microneedles 20 or 120 through the stratum corneum and epidermis, and also into the dermis where the insulin would be absorbed into the capillaries (not shown).

Figure 5A:
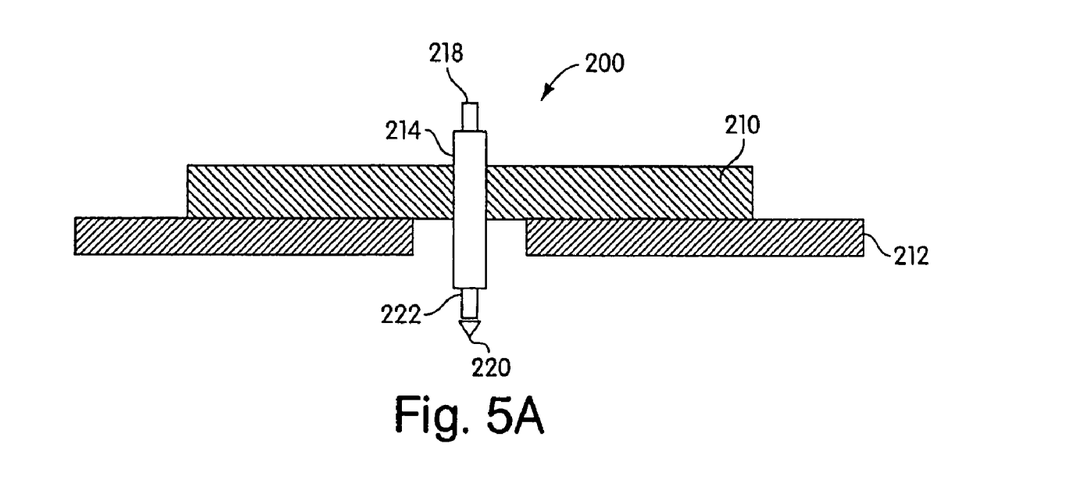
FIGS. 5A and 5B depict a process for clearing tissue from the channel of a microneedle and pumping fluid through the channel.

FIG. 5A depicts a microneedle system 200 that may be employed for delivering a fluid medicant to a patient. More particularly, FIG. 5A depicts a microneedle system 200 that includes a silicon substrate 210, an adhesive patch 212, a microneedle 214, and a pin 218 having an arcuate distal end 220.

As discussed above, the microneedle 200 may be employed by applying the adhesive patch 212 to the skin of a patient. The needle 214 can penetrate through the outer layer of the patient's skin to provide a drug delivery channel. As also discussed above, the distal end 222 of the microneedle 214 may become obstructed, either in part or in whole, by tissue, fluid, or some other material that travels up into an interior channel (not shown) that extends through the microneedle 214. To this end, the microneedle system 200 includes a pin 218 that provides a moveable barrier that is dimensionally adapted for sliding through the interior channel of the microneedle 214 and applying a force to tissue located at the distal end 222 such that the tissue is dislodged from the distal end 222 of the microneedle 214. In the embodiment depicted in FIG. 5A, the pin 218 includes an arcuate tip 220. The arcuate tip 220 is optional and is there to provide the ability to penetrate more deeply into the patient's tissue and thereby move any blocking or obstructing tissue from the distal end 222 of the microneedle into a position that is further away from the microneedle 214. As discussed above the pin 218 may be extendable past the opening of the microneedle to dislodge tissue from the microneedle. However, as discussed above, the pin 218 may also be placed at the distal end of the microneedle 214 as the microneedle is applied to the patient's tissue to block tissue from entering into the interior of the microneedle. In this embodiment, the microneedle 214 is formed as a tube and the pointed distal end 220 of the pin 218 provides the cutting edge that penetrates through the patient's tissue. Optionally however the microneedle 214 may independently have a pointed distal end for penetrating the patient's tissue.

Figure 5B:
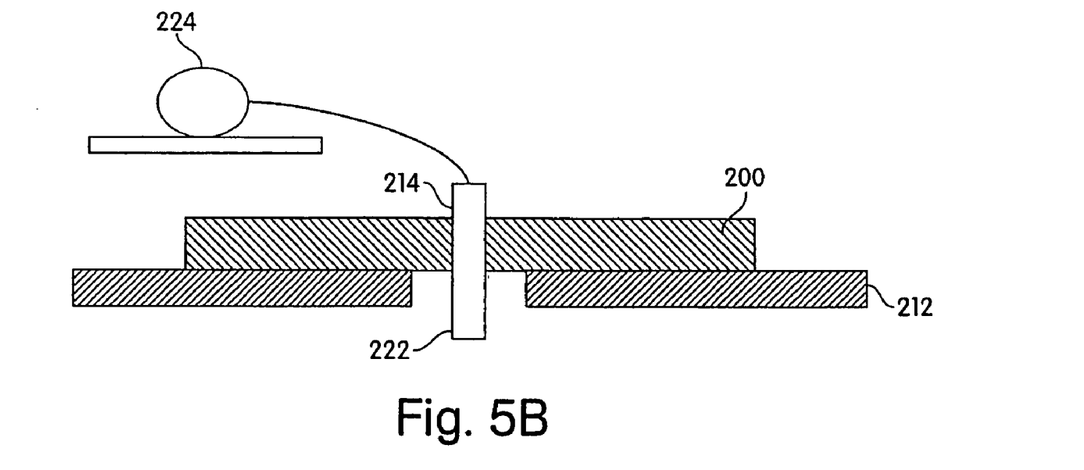
Figure 6A:
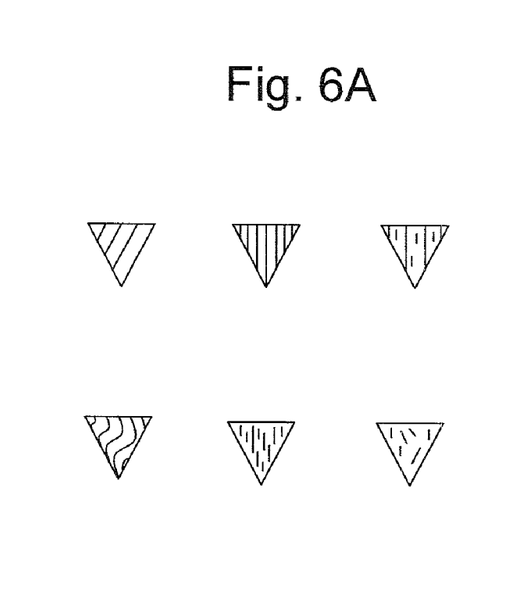
FIG. 6A depicts several head-on views of walls of the interior channels of the microneedles of FIGS. 2A and 2B, and further depicts that the channels are grooved or scored.
Figure 6B:
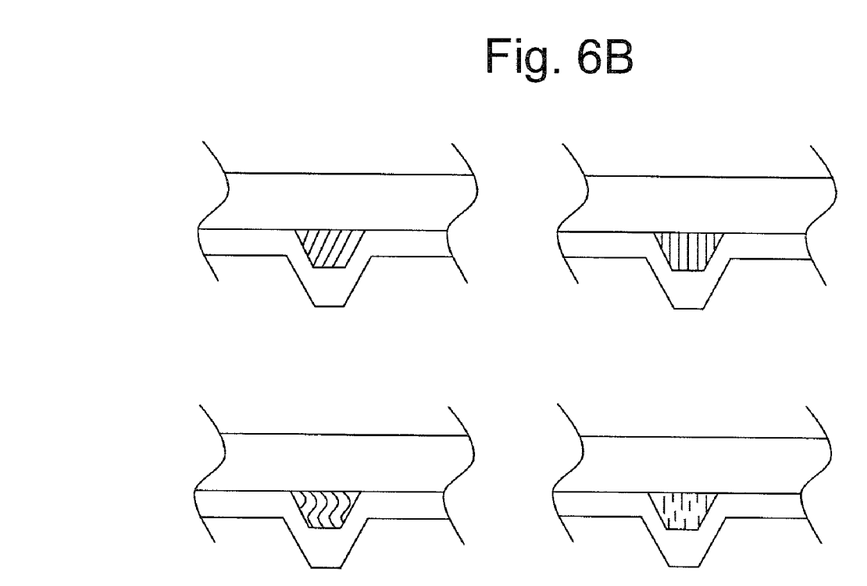
FIG. 6B depicts several cross-sectional views of various microneedle plugs of FIGS. 2A and 2B, and further depicts that the microneedle plugs have an exterior surface that is grooved or scored.

Turning to FIG. 5B, there is depicted another step in the process for delivering the fluid to the patient through the microneedle system 200. Specifically, as shown therein, the pin 218 is removed from the microneedle 214. Once removed, the interior channel is available and may be attached to a pump 224. The pump 224 could be a fluidic piston or pump of a kind commonly employed for delivering a low dosage of medicine to a patient. As depicted in FIG. 5B, the pump 224 can connect to a proximal end of the microneedle 214 to allow for the delivery of fluid through the interior channel and into the patient. In experiments Dosage is delivered through the microneedle 214 as shown in Table 1.

Microneedle Pin insert 218—0.12 mm Diam Seirin Accupuncture Needle; J Type; No. 2; Sterilized with ETO; Lot 0121505; expiration 12/03; Seirin Corp., Shizuoka, JP Microneedle 214 (30 G tube)-304 SS; ID=0.0055"/0.0065"; OD=0.0120"/0.0125"; L=0.155"/0.165"; Micro Tube 30 Ga; Eagle Stainless Tube & Manufacturing, Inc., Franklin, Mass.

Silicone substrate 210—60 mil thick; Die cut ⅜" diam.; Class VI Medical Grade; 60 Shore A; Part No. 87315k65; McMaster-Carr Supply Co.

Adhesive tape 212—Medical Tape 1513; 3M Transparent Polyester 3.4 Mil Double Coated Medical Tape Liquid adhesive—RP 30; Advanced Performance Instant Adhesive; USP Class 6; exp. Aug. 27, 2003; Adhesive Systems Inc., Franklin, Ill.

Tygon tubing—Tygong Flexible Plastic Tubing; ID=0.010"; OD=0.030"; Formulation S-54-HL for surgical and hospital use; Norton Performance Plastics, Akron, Ohio; Lot #133341; Saint-Gobain PPL Corp.

Syringe pump 224—BD 1 ml disposable plastic syringe with hypodermic needle; Becton, Dickinson and Co., Franklin Lakes, N.J.

TABLE 1

| Flow rate (ul/min) | Volume (ul) | Time (min:sec) | Comments |
| --- | --- | --- | --- |
| 1 | 50 | 50:00 | Some pain during insertion; slight stinging begins 6 minutes into the experiment and gradually becomes more painful up until about the 20 min mark, then decreases until it disappears at ~32 min; piston moved ~50 ul; minor leaking upon removal ~1 ul; site does not appear raised immediately after removal, observed after two minutes - skin was slightly raised in 1-2 mm region as evidenced by touch |
| 2 | 50 | 25:00 | No insertion pain; very little sensation during infusion; piston moved ~50 ul; minor leaking upon removal <1 ul (probably spilled from tube); site does not appear raised immediately after removal, site after 2 min was slightly raised, ~2 mm diam, reddened |
| 5 | 50 | 10:00 | Some insertion pain; some stinging during infusion, big pain increase at 8 min, strong stinging/burning sensation; no leaking; site does not appear raise immediately after removal, after 2 min site was slightly raised, ~2 mm diam region, reddened |
| 10 | 50 | 5:00 | No insertion pain; slight infusion pain starts at 2 min; no leaking; site does not appear raised immediately after removal, 2 min after removal site was slightly raised, 2 mm diam, reddened |
| 20 | 50 | 2:30 | Relatively pain free insertion; very low infusion sensation, some pain a few seconds before end of the run; piston moved ~50 ul; no leaking; site is reddened over a 2 mm diam area, but doesn't appear to be raised |
| 40 | 50 | 1:15 | Low pain; no infusion sensation; piston moved ~50 ul; no leaking; site is raised immediately after removal just less than a 1 cm diam region, reddened zone ~1 mm diam. |
| 80 | 50 | 0:37.5 | Painless insertion; stinging during infusion; piston moved ~50 ul; no leaking; site is raised ~ 1 cm diam |
| 160 | 50 | 0:18.75 | Relatively pain free insertion; stinging and cold sensation, ~2 ul leaked when removed tubing from tube; piston moved ~50 ul; site raised to a height ~500 um over an ~1 cm diam region |

Materials:

The above experiment was conducted with a system constructed as depicted in FIGS. 5A and 5B and applied to the underside of a forearm. The data collected and recorded is set out in Table 1 above. The experimental setup was constructed using the following materials, however other materials and components may be substituted by those skill in the art without substantially detracting from the results achieved.

Saline—100 ml bag of 0.9% Sodium Chloride Injection USP; Lot PS 114900; Exp. Apr. 3; Baxter Healthcare Corp., Deerfield, Ill.

Syringe pump 224—Model KDS100; Ser. No. 4736; kdScientific Inc., New Hope, Pa.

Accordingly, as shown in FIGS. 5 and 5B the systems and methods described herein may be employed to increase the amount of medicant or fluid delivered to the patient. In one embodiment, the pump 224 includes a valve and a controller for regulating the flow of fluid through the interior channel and into the patient. Any suitable pump, valve and controller may be employed and the devices selected will depend at least in part on the application. In one embodiment, the pump may be a manually operated pump, such as a syringe. In other embodiments the pump may include a motorized pumping mechanism.

The devices disclosed herein are useful in transport of material into or across biological barriers including the skin (or parts thereof); the blood-brain barrier; mucosal tissue (e.g., oral, nasal, ocular, vaginal, urethral, gastrointestinal, respiratory); blood vessels; lymphatic vessels; or cell membranes (e.g., for the introduction of material into the interior of a cell or cells). The biological barriers can be in humans or other types of animals, as well as in plants, insects, or other organisms, including bacteria, yeast, fungi, and embryos.

The microneedle devices can be applied to tissue internally with the aid of a catheter or laparoscope. For certain applications, such as for drug delivery to an internal tissue, the devices can be surgically implanted.

The microneedle device disclosed herein is typically applied to skin. The skin consists of multiple layers. The stratum corneum is the outer layer (comprising dead cells), generally between 10 and 50 cells for humans, or between 10 and 20 µm thick. Below the stratum corneum is the viable epidermis, which is between 50 and 100 µm thick. The viable epidermis contains no blood vessels, and it exchanges metabolites by diffusion to and from the dermis. Beneath the viable epidermis is the dermis, which is between 1 and 3 mm thick and contains blood vessels, lymphatics, and nerves. The dermis contains a rich capillary network close to the dermal/epidermal junction, and once a drug reaches the dermal depth it diffuses rapidly to deep tissue layers (such as hair follicles, muscles, and internal organs), or systemically via blood circulation.

The microneedle devices disclosed herein include a substrate; one or more microneedles; a reservoir for delivery of drugs; an element for plugging each of the one or more microneedles; and optionally, pump(s), sensor(s), and/or microprocessor(s) to control the interaction of the foregoing.

The substrate of the device can be constructed from a variety of materials, including metals, ceramics, semiconductors, organics, polymers, and composites. The substrate includes the base to which the microneedles are attached or integrally formed. The substrate includes a reservoir for drugs and/or biological molecules.

The microneedles of the device can be constructed from a variety of materials, including metals, ceramics, semiconductors, organics, polymers, and composites. Preferred materials of construction include pharmaceutical grade stainless steel, gold, titanium, nickel, iron, gold, tin, chromium, copper, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes; poly(butyric acid), poly(valeric acid), and poly(lactide-co-caprolactone). Representative non-biodegradable polymers include polycarbonate, polymethacrylic acid, ethylenevinyl acetate, polytetrafluoroethylene (TEFLON™), and polyesters.

Generally, the microneedles should have the mechanical strength to remain intact for delivery of drugs, or serve as a conduit for the collection of biological fluid, while being inserted into the skin, while remaining in place for up to a number of days, and while being removed. In embodiments where the microneedles are formed of biodegradable polymers, however, this mechanical requirement is less stringent, since the microneedles or tips thereof can break off, for example in the skin, and will biodegrade. Nonetheless, even a biodegradable microneedle still needs to remain intact at least long enough for the microneedle to serve its intended purpose (e.g., its conduit function). Therefore, biodegradable microneedles can provide an increased level of safety, as compared to nonbiodegradable ones. The microneedles should be sterilizable using standard methods.

The microneedles of the device may be constructed as described in U.S. Pat. Nos. 6,312,612 and 6,334,856. For example, U.S. Pat. No. 6,312,612 describes a microneedle array constructed of silicon and silicon dioxide compounds using MEMS (i.e., Micro-Electro-Mechanical-Systems) technology and standard microfabrication techniques. The microneedle array may be fabricated from a silicon die which can be etched in a microfabrication process to create hollow cylindrical individual microneedles. One process for manufacturing microneedles described by U.S. Pat. No. 6,312,612 comprises providing a mold comprising a plurality of micropillars that are mounted to a base and differentially melting a thin lay of plastic onto the micropillars, such that the plastic coats the micropillars to form hollow microneedles.

Another example, U.S. Pat. No. 6,334,856 describes microfabrication processes for manufacturing microneedles such as lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination, stereolithography, laser machining, and laser ablation (including projection ablation). See generally Jaeger, Introduction to Microelectronic Fabrication (Addison-Wesley Publishing Co., Reading Mass. 1988); Runyan, et al., Semiconductor Integrated Circuit Processing Technology (Addison-Wesley Publishing Co., Reading Mass. 1990); Proceedings of the IEEE Micro Electro Mechanical Systems Conference 1987-1998; Rai-Choudhury, ed., Handbook of Microlithography, Micromachining & Microfabrication (SPIE Optical Engineering Press, Bellingham, Wash. 1997).

The microneedles of the invention may be hollow. As used herein, the term "hollow" means having one or more substantially annular bores or channels through the interior of the microneedle structure, having a diameter sufficiently large to permit passage of fluid and/or solid materials through the microneedle. The annular bores may extend throughout all or a portion of the needle in the direction of the tip to the base, extending parallel to the direction of the needle or branching or exiting at a side of the needle, as appropriate. One of skill in the art can select the appropriate bore features required for specific applications. For example, one can adjust the bore diameter to permit passage of the particular material to be transported through the microneedle device.

The microneedles can have straight or tapered shafts. A hollow microneedle that has a substantially uniform diameter, which needle does not taper to a point, is referred to herein as a "microtube." As used herein, the term "microneedle" includes both microtubes and tapered needles unless otherwise indicated. In a preferred embodiment, the diameter of the microneedle is greatest at the base end of the microneedle and tapers to a point at the distal end of the microneedle.

The microneedle can also be fabricated to have a shaft that includes both a straight (untapered) portion and a tapered portion.

The microneedles can be formed with shafts that have a circular cross-section in the perpendicular, or the cross-section can be non-circular. For example, the cross-section of the microneedle can be polygonal (e.g. star-shaped, square, triangular), oblong, or another shape. The shaft can have one or more bores. The cross-sectional dimensions typically are between about 10 nm and 1 mm, preferably between 1 micron and 200 microns, and more preferably between 10 and 100 µm. The outer diameter is typically between about 10 µm and about 100 µm, and the inner diameter is typically between about 3 µm and about 80 µm.

The length of the microneedles typically is between about 1 µm and 1 mm, preferably between 10 microns and 500 microns, and more preferably between 30 and 200 µm. The length is selected for the particular application, accounting for both an inserted and uninserted portion. An array of microneedles can include a mixture of microneedles having, for example, various lengths, outer diameters, inner diameters, cross-sectional shapes, and spacings between the microneedles.

The microneedles can be oriented perpendicular or at an angle to the substrate. Preferably, the microneedles are oriented perpendicular to the substrate so that a larger density of microneedles per unit area of substrate can be provided. An array of microneedles can include a mixture of microneedle orientations, heights, or other parameters.

In a preferred embodiment of the device, the substrate and/or microneedles, as well as other components, are formed from flexible materials to allow the device to fit the contours of the biological barrier, such as the skin, vessel walls, or the eye, to which the device is applied. A flexible device will facilitate more consistent penetration during use, since penetration can be limited by deviations in the attachment surface. For example, the surface of human skin is not flat due to dermatoglyphics (i.e. tiny wrinkles) and hair.

The microneedle devices of the invention also include a reservoir in fluid communication with the microneedles. The reservoir is formed in the substrate in a space below the base (to which the microneedles are attached). Typically, the reservoir will accommodate about 0.2-10.0 ml of a solution or a suspension containing a therapeutic agent (e.g., the reservoir can contain about 0.4, 0.5, 1.0, 2.5, 5.0 or 7.5 ml of such a solution). The reservoir and therapeutic agent may be chosen such that the device contains not more than 1, 2, 3, 5, or 10 days supply of the agent.

In a preferred embodiment, the reservoir contains drug, for delivery through the microneedles. The reservoir may be a hollow vessel, a porous matrix, or a solid form including drug which is transported therefrom. The reservoir can be formed from a variety of materials that are compatible with the drug or biological fluid contained therein. Preferred materials include natural and synthetic polymers, metals, ceramics, semiconductors, organics, and composites.

The microneedle device can include one or a plurality of chambers for storing materials to be delivered. In the embodiment having multiple chambers, each can be in fluid connection with all or a portion of the microneedles of the device array. In one embodiment, at least two chambers are used to separately contain drug (e.g., a lyophilized drug, such as a vaccine) and an administration vehicle (e.g., saline) in order to prevent or minimize degradation during storage. Immediately before use, the contents of the chambers are mixed. Mixing can be triggered by any means, including, for example, mechanical disruption (i.e. puncturing or breaking), changing the porosity, or electrochemical degradation of the walls or membranes separating the chambers. In another embodiment, a single device is used to deliver different drugs, which are stored separately in different chambers. In this embodiment, the rate of delivery of each drug can be independently controlled.

In a preferred embodiment, the reservoir should be in fluid communication with the microneedles so that the therapeutic in a fluid composition or form could exit the reservoir and flow into the hollow microneedles.

The microneedle devices of the invention also include one or more elements for plugging each of the one or more microneedles (the plugging element). The plugging element of the device can be constructed from a variety of materials, including metals, ceramics, semiconductors, organics, polymers, and composites. Generally, the plugging element should have the mechanical strength to prevent skin or other tissue from enter the hollow microneedles when the microneedle device is applied to the skin. In a preferred embodiment, the plugging element may comprise a platform, held up by springs, including a plurality of protuberances (microneedle plugs) sized to fit into the hollow microneedles to prevent skin or other tissue barriers from entering the hollow microneedles. As the inner diameter of the microneedles is typically between about 3 µm and about 80 µm, the outer diameter of the microneedle plugs will typically be between about 3 µm and about 80 µm, depending on the diameter of the microneedles. The length of the microneedles typically is between about 1 µm and about 1 mm. The length of the microneedle plugs will also be between about 1 µm and about 1 mm. The microneedle plug may, however, extend past the length of the microneedles. The microneedle plugs also may mimic the perpendicular, cross-sectional shape of microneedles, for example, the perpendicular cross-section of the microneedle plug can be polygonal (e.g. star-shaped, square, triangular), oblong, or another shape best able to fit the microneedle.

In another preferred embodiment, a microneedle device includes a plurality of bioerodible elements (microneedle plugs) for temporarily plugging the hollow microneedles, thereby preventing skin or other tissue barriers from entering the hollow microneedles. The microneedle plug is comprised of a continuous piece of bioerodible polymer having a portion inside and a portion outside the distal end of the microneedle. The portion inside the distal end of the microneedle is held in place by friction or by a small amount of biocompatible adhesive. The microneedle plug also may mimic the perpendicular, cross-sectional shape of microneedle, for example, the perpendicular cross-section of the microneedle plug can be polygonal (e.g. star-shaped, square, triangular), oblong, or another shape best able to fit the microneedle. The portion inside the distal end of the microneedle may be from about 1 µm to about 500 µm in length, preferably from about 1 µm to about 250 µm, more preferably from about 5 µm to about 100 µm. The cross-sectional dimensions of the portion inside the distal end of the microneedle may be from about 10 nm to about 1 mm, preferably from about 1 µm to about 200 µm, more preferably from about 3 µm to about 80 µm.

The portion outside the distal end of the microneedle may have a cone shape with the base (widest portion) of the cone attached to the polymer portion inside the microneedle. The outside portion may be from about 1 µm up to about 500 µm in length and have a diameter at the base from about 1 µm up to about 1.2 mm in diameter. The diameter of the base of the cone will be greater than the diameter of the microneedle to which it is fitted. The outside portion may have an arrowhead shape, the barbed ends of the arrowhead shape extending past the sides of the microneedle. The width of the arrowshead across the barbed ends should be wider than the diameter of the microneedle.

The microneedle devices of the invention also must be capable of transporting material across the barrier at a useful rate. For example, a microneedle device must be capable of delivering drug across the skin at a rate sufficient to be therapeutically useful. A device may include a housing with microelectronics and other micromachined structures to control the rate of delivery either according to a preprogrammed schedule or through active interface with the patient, a healthcare professional, or a biosensor. The rate can be controlled by manipulating a variety of factors, including the characteristics of the drug formulation to be delivered (e.g., its viscosity, electric charge, and chemical composition); the dimensions of each microneedle (e.g., its outer diameter and the area of porous or hollow openings); the number of microneedles in the device; the application of a driving force (e.g., a concentration gradient, a voltage gradient, a pressure gradient); and the use of a valve.

The rate also can be controlled by interposing between the drug in the reservoir and the opening(s) at the base end of the microneedle polymer or other materials selected for their diffusion characteristics. For example, the material composition and layer thickness can be manipulated using methods known in the art to vary the rate of diffusion of the drug of interest through the material, thereby controlling the rate at which the drug flows from the reservoir through a microneedle and into the tissue.

Transportation of molecules through the microneedles can be controlled or monitored using, for example, various combinations of valves, pumps, sensors, actuators, and microprocessors. These components can be produced using standard manufacturing or microfabrication techniques. Actuators that may be useful with the microneedle devices disclosed herein include micropumps, microvalves, and positioners. In a preferred embodiment, a microprocessor is programmed to control a pump or valve, thereby controlling the rate of delivery.

Flow of molecules through the microneedles can occur based on diffusion, capillary action, or can be induced using conventional mechanical pumps or nonmechanical driving forces, such as electroosmosis or electrophoresis, or convection. For example, in electroosmosis, electrodes are positioned on the biological barrier surface, one or more microneedles, and/or the substrate adjacent the needles, to create a convective flow which carries oppositely charged ionic species and/or neutral molecules toward or into the biological barrier. In a preferred embodiment, the microneedle device is used in combination with another mechanism that enhances the permeability of the biological barrier, for example by increasing cell uptake or membrane disruption, using electric fields, ultrasound, chemical enhancers, viruses, pH, heat and/or light.

Passage of the microneedles, or drug to be transported via the microneedles, can be manipulated by shaping the microneedle surface, or by selection of the material forming the microneedle surface (which could be a coating rather than the microneedle per se). For example, the physical surface properties of the microneedle could be manipulated to either promote or inhibit transport of material along the microneedle surface, such as by controlling hydrophilicity or hydrophobicity.

The flow of molecules can be regulated using a wide range of valves or gates. These valves can be the type that are selectively and repeatedly opened and closed, or they can be single-use types. For example, in a disposable, single-use drug delivery device, a fracturable barrier or one-way gate may be installed in the device between the reservoir and the opening of the microneedles. When ready to use, the barrier can be broken or gate opened to permit flow through the microneedles. Other valves or gates used in the microneedle devices can be activated thermally, electrochemically, mechanically, or magnetically to selectively initiate, modulate, or stop the flow of molecules through the needles. In a preferred embodiment, flow is controlled by using a rate-limiting membrane as a "valve."

The microneedle devices can further include a flowmeter or other means to monitor flow through the microneedles and to coordinate use of the pumps and valves.

The microneedle devices of the invention can further include sensors. Useful sensors may include sensors of pressure, temperature, chemicals, and/or electromagnetic fields. Biosensors can be located on the microneedle surface, inside a hollow or porous microneedle, or inside a device in communication with the body tissue via the microneedle (solid, hollow, or porous). These microneedle biosensors can include four classes of principal transducers: potentiometric, amperometric, optical, and physiochemical. An amperometric sensor monitors currents generated when electrons are exchanged between a biological system and an electrode. Blood glucose sensors frequently are of this type.

The microneedle may function as a conduit for fluids, solutes, electric charge, light, or other materials. In one embodiment, hollow microneedles can be filled with a substance, such as a gel, that has a sensing functionality associated with it. In an application for sensing based on binding to a substrate or reaction mediated by an enzyme, the substrate or enzyme can be immobilized in the needle interior.

Wave guides can be incorporated into the microneedle device to direct light to a specific location, or for detection, for example, using means such as a pH dye for color evaluation. Similarly, heat, electricity, light or other energy forms may be precisely transmitted to directly stimulate, damage, or heal a specific tissue or intermediary (e.g., tattoo remove for dark skinned persons), or diagnostic purposes, such as measurement of blood glucose based on IR spectra or by chromatographic means, measuring a color change in the presence of immobilized glucose oxidase in combination with an appropriate substrate.

The microneedle devices can further include a collar or flange, for example, around the periphery of the substrate or the base. It preferably is attached to the device, but alternatively can be formed as integral part of the substrate, for example by forming microneedles only near the center of an "oversized" substrate. The collar can also emanate from other parts of the device. The collar can provide an interface to attach the microneedle array to the rest of the device, and can facilitate handling of the smaller devices.

The device may be attached to the patient by a belt, strap, or adhesive (e.g., it can be attached to the patient's skin by an adhesive patch). In some instances, an adhesive and a second security device (e.g., a belt or strap) can be used.

In a preferred embodiment, a microneedle device includes an adhesive to temporarily secure the device to the surface of the biological barrier. The adhesive can be essentially anywhere on the device to facilitate contact with the biological barrier. For example, the adhesive can be on the surface of the collar (same side as microneedles), on the surface of the substrate between the microneedles (near the base of the microneedles), or a combination thereof.

The microneedle devices of the present invention may be used for single or multiple uses for rapid transport across a biological barrier or may be left in place for longer times (e.g., hours or days) for long-term transport of molecules. Depending on the dimensions of the device, the application site, and the route in which the device is introduced into (or onto) the biological barrier, the device may be used to introduce or remove molecules at specific locations.

In particular embodiments, the device should be "user-friendly." For example, in some transdermal applications, affixing the device to the skin should be relatively simple, and not require special skills. The embodiment of a microneedle may include an array of microneedles attached to a housing containing drug in an internal reservoir, wherein the housing has a bioadhesive coating around the microneedles and the microneedles are plugged with bioerodible elements. The patient can remove a peel-away backing to expose an adhesive coating, and then press the device onto a clean part of the skin, leaving it to administer drug over the course of, for example, several days.

Essentially any drug or other bioactive agents can be delivered using these devices. Drugs can be proteins, enzymes, polysaccharides, polynucleotide molecules, and synthetic organic and inorganic compounds. A preferred drug is insulin. Representative agents include anti-infectives, hormones, growth regulators, drugs regulating cardiac action or blood flow, vaccines, chemotherapy agents, pain relief agents, dialysis-related agents, blood thinning agents, and drugs for pain control. The drug can be for local treatment or for regional or systemic therapy. The following are representative examples, and disorders the drug is used to treat, or the drug's mode of action: calcitonin (osteoporosis), enoxaprin (anticoagulant), etanercept (rheumatoid arthritis), erythropoietin (anemia), fentanyl (postoperative and chronic pain), filgrastin (low white blood cells from chemotherapy), heparin (anticoagulant), insulin (human, diabetes), interferon beta I a (multiple sclerosis), lidocaine (local anesthesia), somatropin (growth hormone), sumatriptan (migraine headaches), vaccines towards tumors, and vaccines towards infectious diseases.

It will be understood that the microneedle device of the present invention can be used in many applications, including as a painless and convenient transdermal drug-delivery system for continuous and controlled outpatient therapies. Another use of the microneedle device of the present invention is to form a portable drug delivery system for outpatient delivery of the following drugs and therapeutic agents, for example: central nervous system therapy agents, psychic energizing drugs, tranquilizers, anticonvulsants, muscle relaxants and anti-parkinson agents, smoking cessation agents, analgesics, antipyretics and anti-inflammatory agents, antispasmodics and antiulcer agents, antimicrobials, antimalarias, sympathomimetric patches, antiparasitic agents, neoplastic agents, nutritional agents, and vitamins.

The devices may contain a predetermined dosage of therapeutic which may be dependent on the disease or disorder being treated, the size of the individual to be treated, the effective dose of the therapeutic, etc.

In this way, many drugs can be delivered at a variety of therapeutic rates. The rate can be controlled by varying a number of design factors, including the outer diameter of the microneedle, the number and size of channels in each microneedle, the number of microneedles in an array, the magnitude and frequency of application of the force driving the drug through the microneedle and/or the holes created by the microneedles. For example, devices designed to deliver drug at different rates might have more microneedles for more rapid delivery and fewer microneedles for less rapid delivery. As another example, a device designed to deliver drug at a variable rate could vary the driving force (e.g., pressure gradient controlled by a pump) for transport according to a schedule which was pre-programmed or controlled by, for example, the user or his doctor. The devices can be affixed to the skin or other tissue to deliver drugs continuously or intermittently, for durations ranging from a few seconds to several hours or days.

One of skill in the art can measure the rate of drug delivery for particular microneedle devices using in vitro and in vivo methods known in the art. For example, to measure the rate of transdermal drug delivery, human cadaver skin mounted on standard diffusion chambers can be used to predict actual rates. See Hadgraft & Guy, eds., Transdermal Drug Delivery: Developmental Issues and Research Initiatives (Marcel Dekker, New York 1989); Bronaugh & Maibach, Percutaneous Absorption, Mechanisms—Methodology—Drug Delivery (Marcel Delker, New York 1989). After filling the compartment on the dermis side of the diffusion chamber with saline, a microneedle array is inserted into the stratum corneum; a drug solution is placed in the reservoir of the microneedle device; and samples of the saline solution are taken over time and assayed to determine the rates of drug transport.

One embodiment of the devices described herein may be used to remove material from the body across a biological barrier, i.e. for minimally invasive diagnostic sensing. For example, fluids can be transported from interstitial fluid in a tissue into a reservoir in the upper portion of the device. The fluid can then be assayed while in the reservoir or the fluid can be removed from the reservoir to be assayed, for diagnostic or other purposes. For example, interstitial fluids can be removed from the epidermis across the stratum corneum to assay for glucose concentration, which should be useful in aiding diabetics in determining their required insulin dose. Other substances or properties that would be desirable to detect include lactate (important for athletes), oxygen, pH, alcohol, tobacco metabolites, and illegal drugs (important for both medical diagnosis and law enforcement).

The sensing device can be in or attached to one or more microneedles, or in a housing adapted to the substrate. Sensing information or signals can be transferred optically (e.g., refractive index) or electrically (e.g., measuring changes in electrical impedance, resistance, current, voltage, or combination thereof). For example, it may be useful to measure a change as a function of change in resistance of tissue to an electrical current or voltage, or a change in response to channel binding or other criteria (such as an optical change) wherein different resistances are calibrated to signal that more or less flow of drug is needed, or that delivery has been completed.

In one embodiment, one or more microneedle devices can be used for (1) withdrawal of interstitial fluid, (2) assay of the fluid, and/or (3) delivery of the appropriate amount of a therapeutic agent based on the results of the assay, either automatically or with human intervention. For example, a sensor delivery system may be combined to form, for example, a system which withdraws bodily fluid, measures its glucose content, and delivers an appropriate amount of insulin. The sensing or delivery step also can be performed using conventional techniques, which would be integrated into use of the microneedle device. For example, the microneedle device could be used to withdraw and assay glucose, and a conventional syringe and needle used to administer the insulin, or vice versa.

Other than transport of drugs and biological molecules, the microneedles may be used to transmit or transfer other materials and energy forms, such as light, electricity, heat, or pressure. The microneedles, for example, could be used to direct light to specific locations within the body, in order that the light can directly act on a tissue or on an intermediary, such as light-sensitive molecules in photodynamic therapy.

The microneedles can also be used for aerosolization or delivery for example directly to a mucosal surface in the nasal or buccal regions or to the pulmonary system.

The microneedle devices disclosed herein also should be useful for controlling transport across tissues other than skin. For example, microneedles could be inserted into the eye across, for example, conjunctiva, sclera, and/or cornea, to facilitate delivery of drugs into the eye. Similarly, microneedles inserted into the eye could facilitate transport of fluid out of the eye, which may be of benefit for treatment of glaucoma. Microneedles may also be inserted into the buccal (oral), nasal, vaginal, or other accessible mucosa to facilitate transport into, out of, or across those tissues. For example, a drug may be delivered across the buccal mucosa for local treatment in the mouth or for systemic uptake and delivery. As another example, microneedle devices may be used internally within the body on, for example, the lining of the gastrointestinal tract to facilitate uptake of orally-ingested drugs or the lining of blood vessels to facilitate penetration of drugs into the vessel wall. For example, cardiovascular applications include using microneedle devices to facilitate vessel distension or immobilization, similarly to a stent, wherein the microneedles/substrate can function as a "staple-like" device to penetrate into different tissue segments and hold their relative positions for a period of time to permit tissue regeneration. This application would be particularly useful with biodegradable devices. These uses may involve invasive procedures to introduce the microneedle devices into the body or could involve swallowing, inhaling, injecting or otherwise introducing the devices in a non-invasive or minimally-invasive manner.

It will also be understood that the length of the individual microneedles is by far the most important dimension with regard to providing a painless and bloodless drug-dispensing system, or a painless and bloodless body-fluids sampling system using the opposite direction of fluid flow. While the dimensions discussed hereinabove are preferred, and the ranges discussed are normal for human skin, it will further be understood that the microneedle arrays of the present invention can be used on skin of any other form of living (or even dead) creatures or organisms, and the preferred dimensions may be quite different as compared to those same dimensions for use with human skin, all without departing from the principles of the present invention.

While the invention has been disclosed in connection with the preferred embodiments shown and described in detail, various modifications and improvements thereon will become readily apparent to those skilled in the art. It should be understood that all matter contained in the above description or shown in the accompanying drawings shall be interpreted as illustrative, and not in a limiting sense, and that the following claims should be interpreted in the broadest sense allowable by law.

The invention claimed is:

1. A microneedle device comprising:

one or more microneedles capable of penetrating the stratum corneum, each of said microneedles comprising an interior channel and a proximal end and a distal end; and a plugging element for plugging one or more of said one or more microneedles, where said plugging element is disposed within the interior channel of one or more of said one or more microneedles;

wherein the plugging element is configured to be removed from the interior channel of the one or more of said one or more microneedles to allow delivery of material across a biological barrier, and wherein the one or more of said one or more microneedles are configured to deliver material only when the plugging element is removed from the interior channel.

2. A microneedle device according to claim 1, further comprising a substrate to which the proximal end of each of said one or more microneedles is affixed.

3. A microneedle device according to claim 2, wherein said plugging element is affixed to said substrate.

4. A microneedle device according to claim 1, wherein said plugging element has a pointed distal end for piercing biological tissue.

5. A microneedle device according to claim 1, further comprising an adhesive.

6. A microneedle device according to claim 1, wherein said one or more microneedles has a perpendicular cross section and said cross section is circular, polygonal, or oblong.

7. A microneedle device according to claim 1, wherein the device comprises microneedles of different lengths.

8. A microneedle device according to claim 1, wherein the device comprises microneedles having interior channels of different diameters.

9. A microneedle device according to claim 1, wherein the device comprises microneedles of different cross-sectional shapes.

10. A microneedle device according to claim 1, further comprising a reservoir in fluid communication with one or more of said one or more microneedles.

11. A microneedle device according to claim 1, further comprising multiple chambers in which material to be delivered is stored.

12. A microneedle device according to claim 1, further comprising one or more elements selected from the group consisting of one or more pumps, one or more sensors, one or more valves, one or more actuators, and one or more microprocessors.

13. A microneedle device according to claim 1, wherein the plugging element mimics the cross-sectional shape of one or more of said one or more microneedles.

14. A microneedle device according to claim 1, wherein the plugging element is configured to remain attached to the microneedle device when it is removed from the interior channel of the one or more of said one or more microneedles.

15. A microneedle device according to claim 1, wherein the plugging element is configured to detach from the microneedle device when it is removed from the interior channel of the one or more of said one or more microneedles.

* * * * *